United States Patent [19]

Delarge et al.

[11] 4,002,629

[45] Jan. 11, 1977

[54] CERTAIN PYRIDINE CARBOXAMIDE DERIVATIVES

[75] Inventors: Jacques E. Delarge, Dolembreux; Leopold N. Thunus, Liege; Charles-Leon Lapiere, Tongeren; Andre H. Georges, Ottignies, all of Belgium

[73] Assignee: A. Christiaens Societe Anonyme, Brussels, Belgium

[22] Filed: Sept. 26, 1975

[21] Appl. No.: 617,127

Related U.S. Application Data

[63] Continuation-in-part of Ser. No. 459,987, April 11, 1974, which is a continuation-in-part of Ser. No. 197,139, Nov. 9, 1971, abandoned.

[30] Foreign Application Priority Data

Nov. 11, 1970 United Kingdom .............. 53675/70

[52] U.S. Cl. .................. 260/268 H; 260/295.5 A; 424/250
[51] Int. Cl.² ........................................ C07D 401/04
[58] Field of Search .............. 260/295.5 A, 268 H

[56] References Cited

UNITED STATES PATENTS 3,904,636   9/1975   Delarge et al. .............. 260/294.8 F

*Primary Examiner*—Alan L. Rotman
*Attorney, Agent, or Firm*—Sughrue, Rothwell, Mion, Zinn & Macpeak

[57] ABSTRACT

This invention relates to compounds of the formula:

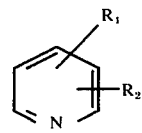

wherein $R_1$ in the 3- or 5-position is a carboxamido group whereas $R_2$ in the 2-position is a 1-methylpiperazinyl group.

Said compounds may be used as anti-inflammatory and cardiovascular agents.

3 Claims, No Drawings

CERTAIN PYRIDINE CARBOXAMIDE DERIVATIVES

This application is a continuation-in-part of our earlier application Ser. No. 459,987 filed on Apr. 11, 1974, in turn a continuation-in-part of Ser. No. 197,139 filed Nov. 9, 1971, now abandoned.

BACKGROUND OF THE INVENTION

The present invention relates to new derivatives of pyridine having valuable pharmacological properties.

According to the present invention, there are provided compounds of formula:

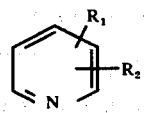

(I)

wherein $R_1$ in the 3- or 5-position of the pyridine nucleus represents a secondary or tertiary carboxamido or carbamyl group when $R_2$ in the 2-position represents a N-methyl-piperazinyl group as well as the pharmaceutically acceptable acid addition salts of the compounds of formula I.

A process for preparing said compounds of formula I comprises reacting a compound of formula:

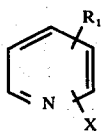

wherein $R_1$ in the 3- or 5-position is as defined hereabove and X in the 2-position represents a halogen group with N-methylpyperazine.

The compounds of this invention may be converted, where possible, into their acid addition salts, preferably hydrochlorides, by conventional methods.

In general formula I, $R_1$ advantageously represents mono- and di-lower alkylcarboxamido, whereas $R_2$ represents N-methyl-piperazinyl.

The compounds of this invention have interesting anti-inflammatory properties.

The anti-inflammatory properties are determined as follows:

The compounds to be tested are given as freshly prepared solutions or suspensions by oral route one hour before injecting the paw with carrageenan, a known inflammatory agent.

The inflammatory agent either in aqueous solution or suspension is then injected into the plantar tissue of the right hind paw of each rat, the left paw remaining untreated and serving as control. Each animal receives for example 0.05ml of an aqueous solution containing 1 % of carrageenan and 0.9 % of sodium chloride.

4 hours after injection, the importance of swelling is determined by plethysmography and is expressed as a percent of the volume of the control paw.

The anti-inflammatory effect expressed as a percent of inhibition is obtained by comparison between rats treated with the anti-inflammatory agent and a control group of rats.

The results of the test for anti-inflammatory activity are given in table I.

TABLE I

| Ref No. | Compound of Example | Acute oedema induced by carrageenan % of inhibition |
|---|---|---|
| 137 | 3 | 51,2 |
| 139 | 5 | 44,4 |
| 141 | 6 | 40,0 |
| 150 | 10 | 32,0 |
|  | Phenylbutazone | 41 |
|  | Methiazinic acid | 46 |
|  | Acetosalicylic acid | 0 |
|  | Flufenamic acid | 34 |
|  | Niflumic acid | 32 |

N.B. 100 mg/kg of anti-inflammatory agent are administered by oral route.

According to a further feature of the present invention, we thus provide pharmaceutical compositions comprising as active ingredient, at least one compound according to the present invention, together with a pharmaceutical carrier or excipient. The compositions are generally intended for peroral rectal or parenteral administration and also for external use. Pharmaceutical compositions for oral administration may, for example, be in the form of dosage units such as tablets, dragees or capsules in which at least one of the compounds according to the invention is mixed with a solid pharmaceutical carrier or excipient.

The compositions according to the present invention can also be used in the form of liquid preparations for oral administration especially syrups, elixirs, aqueous dispersions or solutions.

The compositions according to the present invention can also be in the form of solutions for parenteral administration. Solutions or suspensions for injections can be prepared by using, for example, distilled water in which at least one compound employed as active ingredient is dissolved or suspended, if desired, in the presence of a solubilizing agent.

The compositions according to the present invention may also be formulated for rectal administration, for example, the active ingredient in a suppository base.

The anti-inflammatory compositions according to this invention may also be applied for external use, for example, the active ingredient in an ointment base.

The compounds employed as active ingredients in the compositions according to the invention can be administered in varying doses depending on the particular compound being used, the condition of the patient, and the route of administration.

In general, however, the compounds can be administered orally or rectally in doses of from 50 to 1000 mg to be taken one to four times per day, or parenterally in a single dose of 20 to 500 mg per day.

DETAILED DESCRIPTION OF THE INVENTION

EXAMPLE 1

Preparation of 2-(4'-methyl-1'-piperazinyl)-pyridine-3-diethylcarboxamide and the hydrochloride thereof.

a. 2-chloropyridine-3-diethylcarboxamide is first prepared by either of the following methods:

Method 1:

The following mixture is placed into a 100 ml flask provided with two hecks: 10 g of diethyl-nicotinamide-1-oxide and 50 ml of $OPCl_3$. The mixture is heated to 120° C and 30 g of $PCl_5$ are added little by little. The temperature is maintained at 120° C for 1.5 hour. After cooling, the $OPCl_3$ is evaporated under reduced pressure. The oily residue is poured onto ice and neutralized with NaHCO₃. It is extracted with CHCl₃. The chloroformic solution is evaporated under reduced pressure and the residue is distilled off in vacuo. The desired 2-chloro-diethylcarboxamide passes at 150°–155° C under 0.4–0.5 mm of Hg. Yield: 60 %.
Method 2:

The following mixture is refluxed for 3 hours: 10 g of 2-chloro-nicotinic acid and 80 ml of thionyl chloride. The reaction mixture is evaporated to dryness, extracted with 100 ml of hexane, again evaporated to dryness and the same operation is repeated two further times. The residue is extracted with 50 ml of acetone and the solution thus obtained is poured dropwise and with stirring into a mixture of 20 ml of diethylamine and 80 ml of benzene. After addition, the reaction mixture is evaporated under reduced pressure. The residue is added with water and sodium hydroxide and then extracted with CHCl₃. The chloroformic solution is dried on dry Na₂SO₄ and evaporated under reduced pressure. The residue is distilled in vacuo. The desired 2-chloro-diethylcarboxamide passes at 150°–155° C under 0.4–0.5 mm of Hg.

Elementary analysis:
  % Calculated: C 56,47; H 6,12; N 13,18; Cl 16,70.
  % Found: C 56,34; H 6,23; N 13,29; Cl 16,69.

b. The desired 2-(4'-methyl-1'-piperazinyl)-pyridine-3-diethylcarboxamide is then prepared as follows: 10 g of 2-chloropyridine-3-diethylcarboxamide, 30–40 ml of toluene and 10 g of 1-methyl-piperazine are placed in a 100 ml flask. The reaction mixture is refluxed for 4 hours. A solution is thus obtained and is evaporated under reduced pressure. The residue is taken with H₂O and NaOH and is then extracted with CHCl₃. The chloroformic extracts are evaporated under reduced pressure and the residue thereof is distilled in vacuo. The product passes at about 175° C under 0.4-0.5 mm of Hg. It is taken or extracted with anhydrous acetone and dry gaseous HCl is bubbled through the acetonic solution. The desired product precipitates as its hydrochloride.
Yield: 70 %; m.p. 225°–226.5° C.
Elementary analysis:
  % Calculated: C 57,58; H 8,00; N 17,98.
  % Found: C 57,79; H 8,09; N 17,82.

EXAMPLE 2

Preparation of 2-(4'-methyl-1'-piperazinyl)-pyridine-5-diethylcarboxamide and the hydrochloride thereof.

The method of Example 1b is applied, using 2-chloropyridine-5-diethylcarboxamide as starting material and refluxing the reaction mixture for 8 hours.

Upon distillation, the desired product passes at 220°–230° C under 1.5 mm of Hg.

The hydrochloride thereof is precipitated in the same way as in Example 1.

Examples 3–6

These examples illustrate the preparation of the following products:
2-(4'-methyl-1'-piperazinyl)-pyridine-3-methylcarboxamide (Example 3)
2-(4'-methyl-1'-piperazinyl)-pyridine-3-dimethylcarboxamide (Example 4)
2-(4'-methyl-1'-piperazinyl)-pyridine-3-ethylcarboxamide (Example 5)
2-(4'-methyl-1'-piperazinyl)-pyridine-3-isopropylcarboxamide (Example 6).

These products are prepared by the following general method:

A mixture of 10 g of starting chlorinated compound of formula II, 30–40 ml of toluene and 10 g of N-methylpiperazine is heated and boiled under reflux conditions for 4 hours. After cooling, the solution is evaporated under reduced pressure to obtain an oil. 20 ml water and 20 ml NaOH are added and the mixture is extrated with chloroform. The extraction mixture is then dried and distilled.

Particulars of the compounds are set out in the following table.

TABLE II

Starting product of formula II

| $R_1$ | Compound of Example obtained | Boiling point ° C/mm | Yield | Melting point ° C |
|---|---|---|---|---|
| CONHCH₃ | 3⁽¹⁾ | 184–187° /0,5 | 60 | 95–97 |
| CON(CH₃)₂ | 4⁽²⁾ | 185–190° /1 | 60 | 235 |
| CONHC₂H₅ | 5⁽¹⁾⁽³⁾ | 185–190°/0,8 | 60 | 69 |
| CONHCH(CH₃)₂ | 6⁽¹⁾ | 187–192° /0,5 | 70 | 81 |

⁽¹⁾crystallizes at rest
⁽²⁾precipitated as hydrochloride from a solution in acetone by means of gaseous hydrochloride
⁽³⁾distilled under nitrogen blanket

EXAMPLES 7–10

These examples illustrate the preparation of the following products:
2-(4'-methyl-1'-piperazinyl)-5-methylcarboxamide (Example 7)
2-(4'-methyl-1'-piperazinyl)-5-dimethylcarboxamide (Example 8)
2-(4'-methyl-1'-piperazinyl)-5-ethylcarboxamide (Example 9)
2-(4'-methyl-1'-piperazinyl)-5-isopropylcarboxamide (Example 10)

These products are prepared by the following general method:

A mixture of 10 g of chlorinated starting compound of formula II, 30 to 40 ml of toluene and 10 g of N-methylpiperazine is heated and boiled under reflux conditions during 4 hours. After cooling, the solution thus obtained is evaporated under reduced pressure. 20 ml water and 20 ml NaOH (10 %) are added and the resulting mixture is extracted with CHCl₃. The extraction solution is dried and then evaporated under reduced pressure. The residue is taken up with petroleum ether and stirred until it crystallizes. The solid product is filtered and then crystallized from petroleum ether.

Particulars of the compounds are set out in the following table:

TABLE III

Starting compounds of formula II

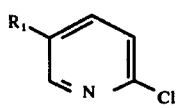

| $R_1$ | Product of Example obtained | Melting point °C | Yield % | Analysis C | H | N |
|---|---|---|---|---|---|---|
| $CONHCH_3$ | 7 | 112–113 | 60 | 61,54 | 7,69 | 23,93 |
|  |  |  |  | 61,48 | 7,71 | 23,75 |
| $CON(CH_3)_2$ | 8 | 86,5–87,5 | 60 | 62,90 | 8,06 | 22,58 |
|  |  |  |  | 62,70 | 8,25 | 22,65 |
| $CONHC_2H_5$ | 9 | 85–97 | 70 | 62,90 | 8,06 | 22,58 |
|  |  |  |  | 62,75 | 8,15 | 22,75 |
| $CONHC_3H_7 iso$ | 10 | 145–146 | 70 | 64,12 | 8,40 | 21,37 |
|  |  |  |  | 64,03 | 8,39 | 21,50 |

(1) Calculated
(2) Found

EXAMPLE 11

Dragees :
Core :
| | |
|---|---|
| Compound of formula I | 50,0 mg |
| Colloïdal silica | 5,0 mg |
| Lactose | 42,5 mg |
| Polyvidone | 3,5 mg |
| Glycerol | 0,5 mg |
| Maize starch | 8,0 mg |
| Talc | 10,0 mg |
| Magnesium stearate | 0,5 mg |

Coating
| | |
|---|---|
| Gum lac | 2,0 mg |
| Gum arabic | 5,4 mg |
| New-Coccine | 0,1 mg |
| Talc | 13,0 mg |
| Colloïdal silica | 9,5 mg |
| Saccharose | 50,0 mg |
| | for one dragee |

EXAMPLE 12

Tablets :
Core :
| | |
|---|---|
| Compound of formula I | 200,0 mg |
| Colloïdal silica | 17,0 mg |
| Stearic acid | 4,0 mg |
| Gelatine | 4,0 mg |
| Glycerol | 1,6 mg |
| Maize starch | 52,0 mg |
| Magnesium stearate | 1,4 mg |
| | for one tablet |

EXAMPLE 13

Capsules :
| | |
|---|---|
| Compound of formula I | 100,0 mg |
| Lactose | 120,0 mg |
| Rice starch | 30,0 mg |
| Maize starch | 30,0 mg |
| Magnesium stearate | 5,0 mg |
| Gelatine } envelope | 78,0 mg |
| Tartrazine } | 0,2 mg |
| | for one capsule |

EXAMPLE 14

Suppositories :
| | |
|---|---|
| Compound of formula I | 300 mg |
| Witepsol H 12 mass ( ) | 600 mg |
| | for one suppository |

( ) a mixture of triglycerides and partial glycerides of saturated fatty acids ($C_{12}$-$C_{18}$) originating from plants, furnished by Dynamit Nobel AG, Koln-Mulheim, Western Germany.

EXAMPLE 15

Vials :
| | |
|---|---|
| Compound of formula I | 20,0 mg |
| Natrium chloride | 85,0 mg |
| Distilled water to form | 10,0 ml |
| | for one vial |

What we claim is:
1. Compounds of the formula:

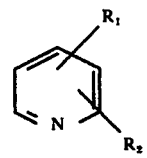

wherein $R_1$ in the 3- or 5-position of the pyridine nucleus represents carboxamido, lower alkyl carboxamido or di-lower alkyl carboxamido group; and $R_2$ in the 2-position represents the N-metyl-piperazinyl group, and the pharmaceutically acceptable salts of the compounds of formula I.

2. A compound according to claim 1, wherein $R_1$ in the 3-position represents methylcarboxamido, ethylcarboxamido or isopropylcarboxamido.

3. A compound according to claim 1, wherein $R_1$ in the 5-position represents dimethylcarboxamido or isopropylcarboxamido.

* * * * *